US00PP31492P3

(12) United States Plant Patent
van Langen

(10) Patent No.: US PP31,492 P3
(45) Date of Patent: Feb. 25, 2020

(54) ***ECHEVERIA* PLANT NAMED 'TSAECH1806'**

(50) Latin Name: ***Echeveria* hybrid**
Varietal Denomination: TSAECH1806

(71) Applicant: Tosjami B.V., Heerhugowaard (NL)

(72) Inventor: Gerard van Langen, Heerhugowaard (NL)

(73) Assignee: Tosjami B.V., Heerhugowaard (NL)

( * ) Notice: Subject to any disclaimer, the term of this patent is extended or adjusted under 35 U.S.C. 154(b) by 0 days.

(21) Appl. No.: 16/501,052

(22) Filed: Feb. 13, 2019

(65) Prior Publication Data

US 2019/0313565 P1 Oct. 10, 2019

(30) Foreign Application Priority Data

Apr. 6, 2018 (QZ) ..... PBR 2018/0956

(51) Int. Cl.
*A01H 5/12* (2018.01)
*A01H 6/00* (2018.01)
*A01H 6/32* (2018.01)

(52) U.S. Cl.
USPC ..... Plt./373
CPC ..... *A01H 6/00* (2018.05); *A01H 5/12* (2013.01); *A01H 6/32* (2018.05)

(58) Field of Classification Search
USPC ..... Plt./373
CPC ..... A01H 5/12
See application file for complete search history.

*Primary Examiner* — Kent L Bell
(74) *Attorney, Agent, or Firm* — Samuel R. McCoy, Jr.

(57) ABSTRACT

A new and distinct *Echeveria* plant named 'TSAECH1806' which is characterized by a dark brown to near-black rosette of succulent foliage which is centered green, as well as the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* disclosed herein has been given the variety denomination 'TSAECH1806'.

CROSS REFERENCE TO RELATED APPLICATIONS

This application claims priority to the Community Plant Variety Rights application number 2018/0956, filed Apr. 6, 2018, which is herein incorporated by reference.

BACKGROUND OF THE INVENTION

Parentage: 'TSAECH1806' is a seedling selection resulting from the controlled pollination of an unnamed and unpatented *Echeveria affinis* plant, the seed parent, with an unnamed and unpatented *Echeveria atropurpurea* plant, the pollen parent. The crossing was made by the inventor in the spring of 2015 at a commercial greenhouse in Heerhugowaard, the Netherlands. In the summer of 2016, one seedling resulting from said cross of 2015 was observed to exhibit unique growth and foliage characteristics and was isolated for further evaluation in order to confirm the distinctness and stability of the characteristics first observed. Upon confirmation of distinctness and stability, 'TSAECH1606' was selected for commercialization.

Asexual Reproduction: Asexual reproduction of the new cultivar 'TSAECH1806', by way of rooting leaf cuttings, was first initiated in the spring of 2017 at the inventor's commercial greenhouse in Heerhugowaard, the Netherlands.

Through three subsequent generations, the unique features of this cultivar have proven to be stable and true to type.

SUMMARY OF THE INVENTION

The cultivar 'TSAECH1806' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'TSAECH1806'. These characteristics in combination distinguish 'TSAECH1806' as a new and distinct *Echeveria* cultivar:

1. 'TSAECH1806' exhibits long, obovate to oblanceolate succulent foliage arranged in a stemless basal rosette; and
2. 'TSAECH1806' exhibits a rosette of foliage which is dark brown to near-black foliage, suffused with greyed-purple, and centered yellow-green; and
3. 'TSAECH1806' exhibits slightly concave foliage; and
4. 'TSAECH1806' exhibits foliage which becomes darker, with less yellow-green coloration at the base, when exposed to high levels ultraviolet light.

BOTANICAL DESCRIPTION OF THE PLANT

Figure 1:
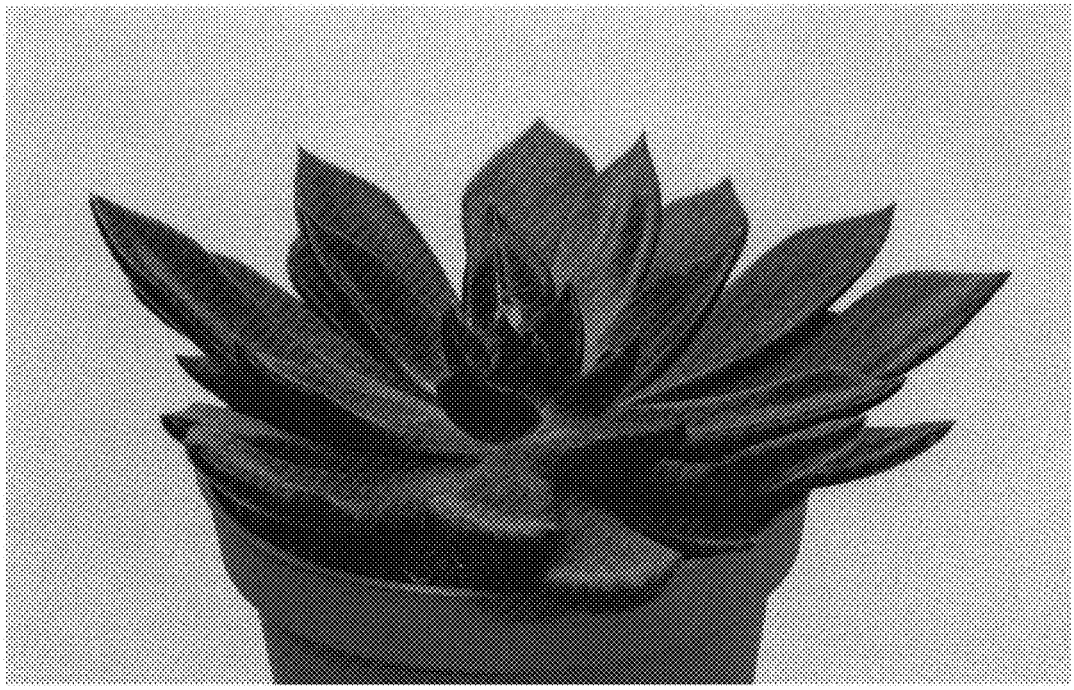
FIG. 1 illustrates, as nearly true as it is reasonably possible to make the same in color photographs of this type, an exemplary plant of 'TSAECH1806' grown in a commercial greenhouse in Heerhugowaard, the Netherlands. This plant is approximately 12 months old, shown planted in a 10.5 cm container.
Figure 2:
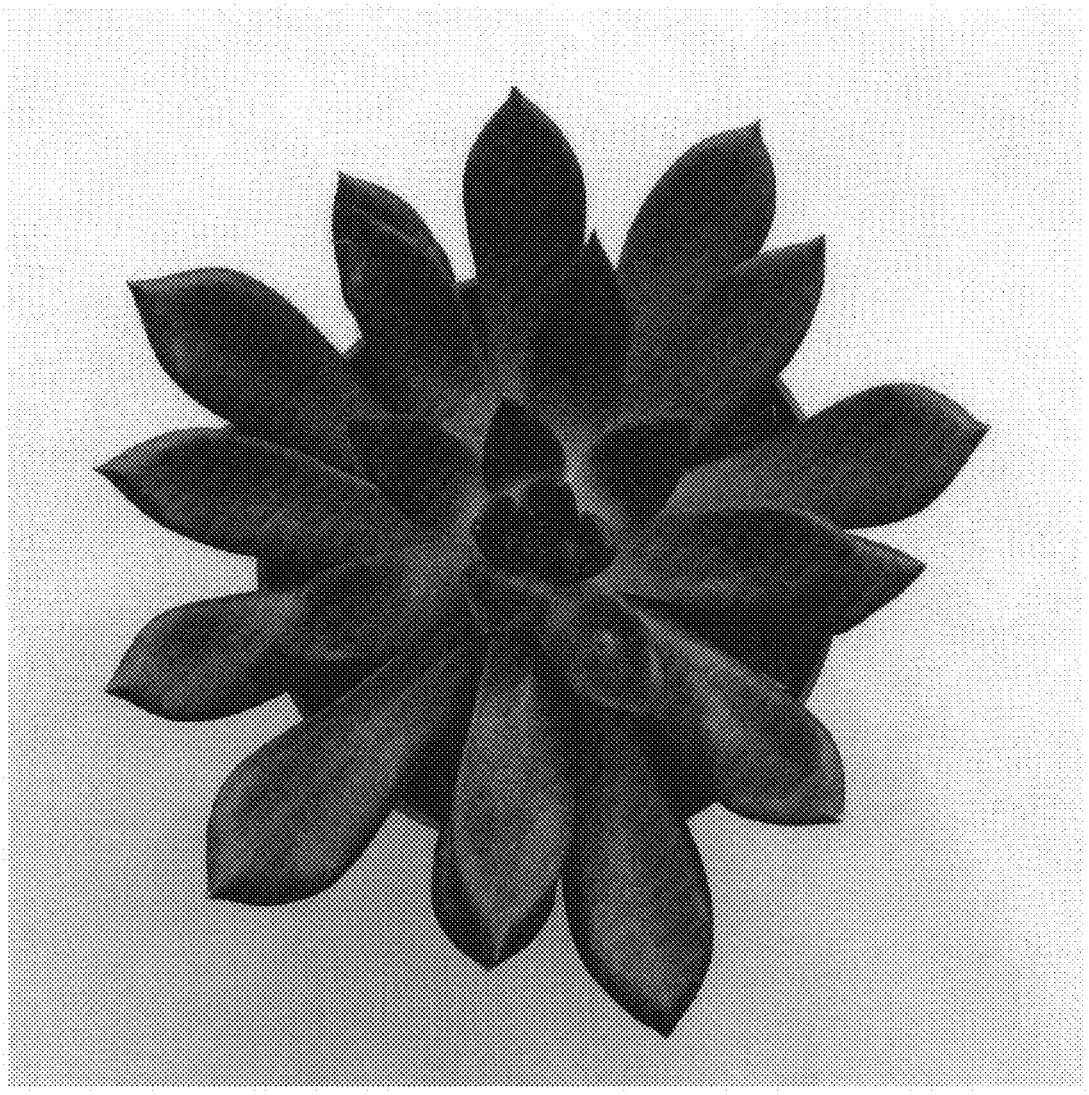
FIG. 2 illustrates, as nearly true as it is reasonably possible to make the same in color photographs of this type, the typical foliage arrangement of 'TSAECH1806'.
Figure 3:
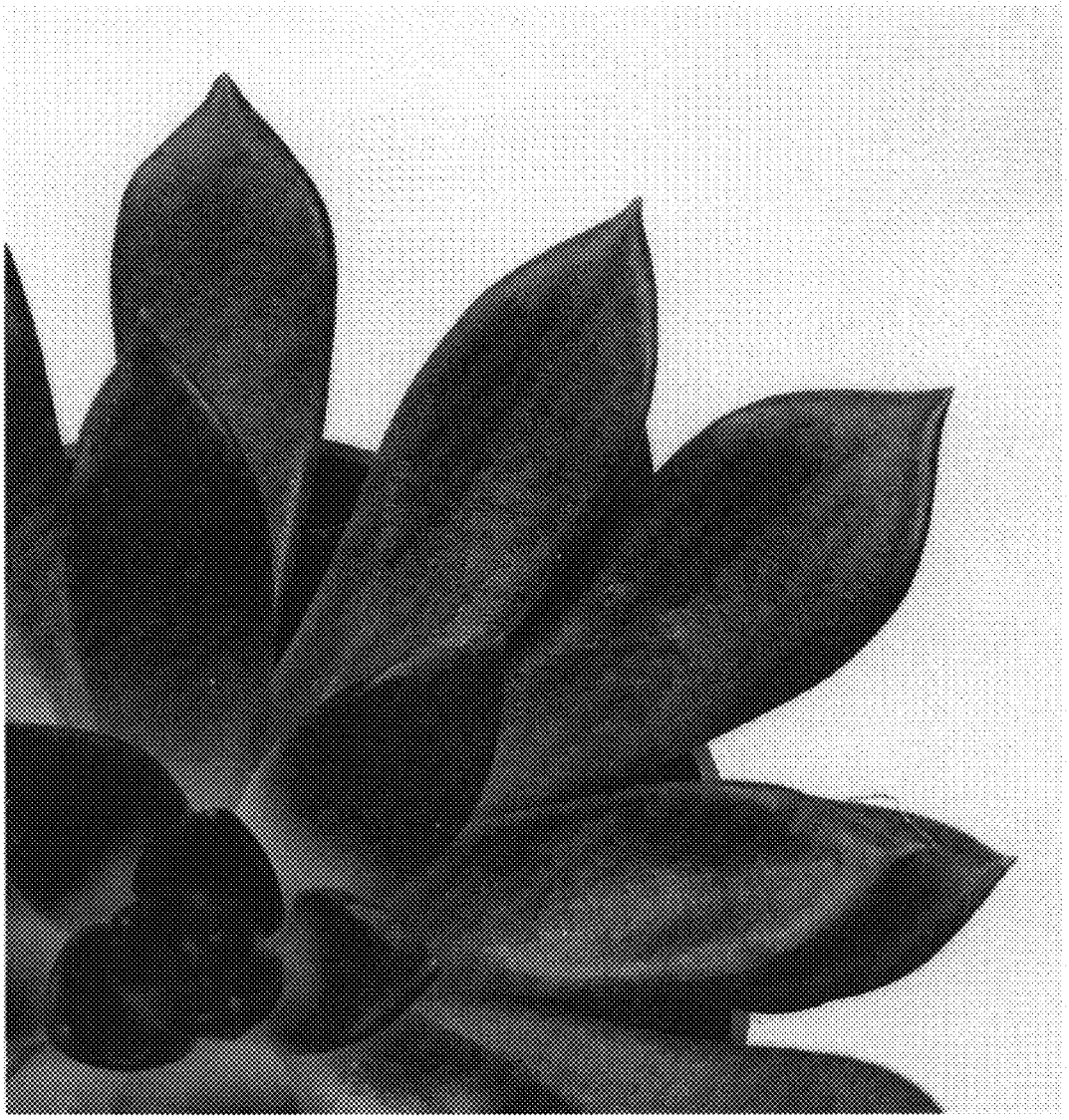
FIG. 3 illustrates, as nearly true as it is reasonably possible to make the same in color photographs of this type, the adaxial surface of the juvenile and mature foliage of 'TSAECH1806'.
Figure 4:
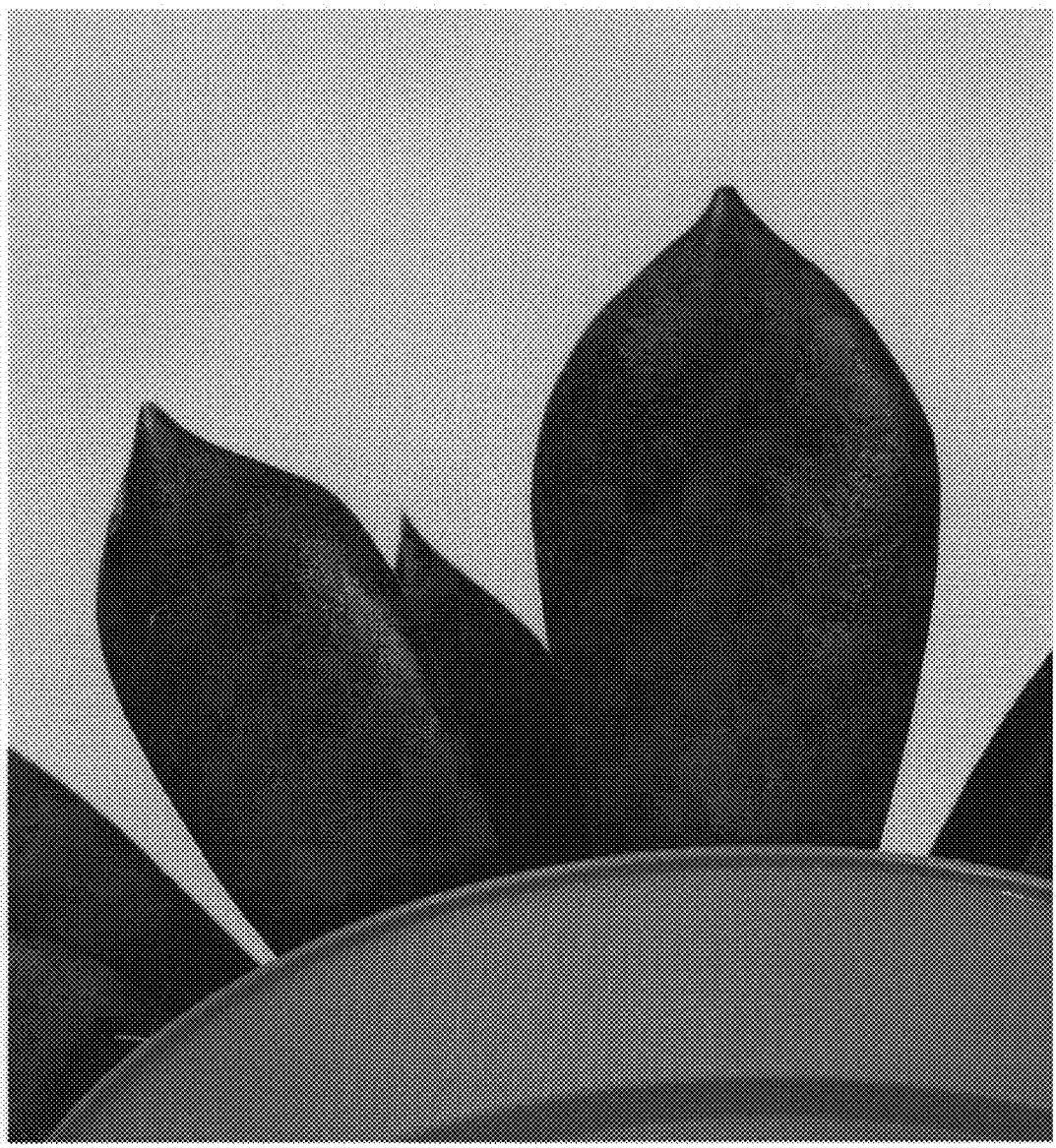
FIG. 4 illustrates, as nearly true as it is reasonably possible to make the same in color photographs of this type, the abaxial surface of the mature foliage of 'TSAECH1806'.

The following observations and measurements made in December of 2018 describe averages from a sample set of six specimens of 12 months old 'TSAECH1806' plants grown in 10.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'TSAECH1806' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'TSAECH1806' and comparisons with the parent plants and closest known comparator are provided below.

Plant description:

*Growth habit*.—Succulent perennial with foliage growing in a stemless basal rosette.

*Plant shape*.—Flattened.

*Height from soil level to top of foliar plane*.—5.2 cm.

*Plant spread*.—Average of 16.2 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 30 weeks to produce a marketable plant in a 10.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Foliage:

*Arrangement*.—Rosette.

*Division*.—Simple.

*Attachment*.—Sessile.

*Quantity*.—Approximately 30 leaves per rosette.

*Shape*.—Obovate to oblanceolate.

*Dimensions*.—7.7 cm long, 2.4 cm wide, and 0.6 cm thick, on average.

*Aspect*.—Slightly concave and slightly curved upwards.

*Attitude*.—Juvenile foliage at the center of the rosette is held outward; foliage becomes progressively more relaxed towards the outer whorls of mature foliage, at an average angle of 15 degrees to horizontal.

*Apex*.—Apiculate.

*Base*.—Long cuneate.

*Margin*.—Entire; lightly undulated.

*Pubescence, texture and luster of the adaxial surface*.—Glabrous, smooth, and glossy; glaucous.

*Pubescence, texture and luster of the abaxial surface*.—Glabrous, smooth, and gloss; glaucous.

*Color*.—Juvenile foliage, adaxial surface — Brown, nearest to RHS 200A, and transitioning to yellow-green towards the base, nearest to a mixture of RHS 145B, 145C, and 145D; the epicuticular wax covering the leaf surface is brown, nearest to RHS 200B. Juvenile foliage, abaxial surface — Brown, nearest to RHS 200B, and transitioning to yellow-green towards the base, nearest to a mixture of RHS 145B, 145C, and 145D; the epicuticular wax covering the leaf surface is brown, nearest to RHS 200B. Mature foliage, adaxial surface — Brown, nearest to in between RHS 200A and 200B, and lightly suffused with greyed-purple, nearest to RHS N186C; transitioning to yellow-green towards the base, nearest to RHS 147D; the epicuticular wax covering the leaf surface is brown, nearest to RHS 200B. Mature foliage, abaxial surface — Greyed-brown, nearest to RHS 187A, and lightly suffused with brown, nearest to RHS 200B; transitioning to yellow-green towards the base, nearest to a mixture of RHS 148C and 148D; the epicuticular wax covering the leaf surface is brown, nearest to RHS 200B.

*Venation*.—No venation is visible.

*Petiole*.—No petiole; leaves are sessile.

*Inflorescence*.—No flowering has been observed to date.

COMPARISONS WITH THE PARENT PLANT AND CLOSEST KNOWN COMPARATOR

Plants of the new cultivar 'TSAECH1806' differ from the seed parent, an unnamed *Echeveria affinis* plant (not patented), in the following characteristics described in Table 1 below.

TABLE 1

| Characteristic | 'TSAECH1806' | Seed parent |
|---|---|---|
| Growth habit. | Less compact. | More compact. |
| General coloration of the foliage. | Less yellow-green is present at the leaf base; less green coloration at the center of the rosette. | More yellow-green is present at the leaf base; more green coloration at the center of the rosette. |

Plants of the new cultivar 'TSAECH1806' differ from the pollen parent, an unnamed *Echeveria atropurpurea* plant (not patented), in the following characteristics described in Table 2 below.

TABLE 2

| Characteristic | 'TSAECH1806' | Pollen parent |
|---|---|---|
| Growth habit. | Stemless rosette. | Foliage born on a stem. |
| Foliage aspect. | Slightly concave and slightly curved upwards. | Strongly concave and strongly curved upwards. |
| Foliage length. | Longer than the pollen parent. | Shorter than 'TSAECH1806'. |
| General coloration of the foliage. | Generally appearing as dark brown to black, suffused with greyed-purple. | Generally appearing as a mixture of brown and dark red. |
| Foliage, margin color. | No distinct margin coloration. | Very thinly margined white. |

COMPARISONS WITH THE CLOSEST KNOWN COMPARATOR

Plants of the new cultivar 'TSAECH1806' differ from the closest known commercial comparator, the common form of *Echeveria* sp. 'Black Prince' (not patented), in the following characteristics described in Table 3 below.

TABLE 3

| Characteristic | 'TSAECH1806' | 'Black Prince' |
|---|---|---|
| Growth habit. | Stemless rosette. | Foliage born on a stem. |
| Foliage shape. | Slightly concave and slightly curved upwards. | Strongly concave and strongly curved upwards. |
| Foliage dimensions. | Longer and more narrow than 'Black Prince'. | Shorter and broader than 'TSAECH1806'. |
| General coloration of the foliage. | Generally appearing as dark brown to black, suffused with greyed-purple. | Generally appearing as a mixture of dark brown to black and red. |

That which is claimed is:

1. A new and distinct variety of *Echeveria* plant named 'TSAECH1806', substantially as described and illustrated herein.

* * * * *